United States Patent [19]

Stec et al.

[11] Patent Number: 5,151,510

[45] Date of Patent: Sep. 29, 1992

[54] METHOD OF SYNETHESIZING SULFURIZED OLIGONUCLEOTIDE ANALOGS

[75] Inventors: Wojciech J. Stec; Bogdan Uznanski, both of Lodz, Poland; B. John Bergot, Redwood City, Calif.; Bernard L. Hirschbein, San Francisco, Calif.; Karen L. Fearon, Union City, Calif.

[73] Assignee: Applied Biosystems, Inc., Foster City, Calif.

[21] Appl. No.: 512,644

[22] Filed: Apr. 20, 1990

[51] Int. Cl.$^5$ .................... C07H 15/12; C07H 17/00; A01N 43/04; C12Q 1/68
[52] U.S. Cl. ........................... 536/27; 536/28; 536/29; 514/12; 514/44; 435/6; 435/172.1
[58] Field of Search ............... 536/27, 28, 29; 435/6, 435/172.1; 514/44, 45, 46, 47, 48, 71, 12

[56] References Cited

U.S. PATENT DOCUMENTS 4,725,677  2/1988  Köster et al. .................. 536/27

FOREIGN PATENT DOCUMENTS

89/11486  11/1989  World Int. Prop. O. .

OTHER PUBLICATIONS

Agrawal et al. (Oct. 1989) PNAS vol. 86, pp. 7790-7794.
Stein et al. (1988) Nucleic Acids Research vol. 16, pp. 3209-3221.
Jacobson et al, J. Amer. Chem. Soc., vol. 77, pp. 6064-6065 (1955).
Bloch, Editor, Annals of the N.Y. Acad. Sci., vol. 255, excerts (1975).
Kornberg et al, DNA Replication, 2nd Ed. (Freeman, San Francisco, 1991), pp. 446-451.
Scheit, Nucleotide Analogs (Wiley, New York, 1980) excerpts.
Iyer et al, J. Org. Chem., vol. 55, pp. 4693-4699 (1990).
Tolmacheva et al, J. of Gen. Chem. of the USSR, vol. 48, pp. 982-984 (1978).
Michalski et al, Roczniki Chemii, vol. 33, pp. 247-250 (1958).
Matsukura et al, Gene, vol. 72, pp. 343-347 (1988).
Iyer et al, J. Am. Chem. Soc., vol. 112, pp. 1253-1254 (1990).
Kamer et al, Tetrahedron Letters, vol. 30, pp. 67576760 (1989).

Primary Examiner—David L. Lacey
Assistant Examiner—Gian P. Wang
Attorney, Agent, or Firm—Stephen C. Macevicz

[57] ABSTRACT

A method for synthesizing sulfurized oligonucleotide analogs, such as phosphorothioate and phosphorodithioate analogs, is provided that employs a thiophosphorus compound, such as a thiophosphoric, dithiophosphoric, thiophosphinic, or dithiophosphinic acid disulfide or polysulfide, as a sulfurizing agent. The method of the invention may be used to sulfurize any phosphorous-(III)-containing intermediate. Preferably, the method is practiced on a commercial DNA synthesizer using phosphoramidite and/or phosphorthioamidite intermediates.

17 Claims, No Drawings

METHOD OF SYNETHESIZING SULFURIZED OLIGONUCLEOTIDE ANALOGS

FIELD OF THE INVENTION

The invention relates generally to the synthesis of oligonucleotides, and more particularly, to a method for sulfurizing oligonucleotides with thiophosphorus compounds to form oligodeoxyribonucleoside phosphorothioates and/or phosphorodithioates.

BACKGROUND

With the development of efficient methods of synthesis, interest has arisen in the use of anti-sense oligonucleotides to treat a variety of diseases, particularly viral infections, e.g. Matsukura et al, Proc. Natl.Acad.Sci., Vol. 86, pgs. 4244-4448 (1989). An antisense oligonucleotide is a synthetic oligonucleotide of varying length, usually in the range of about 12 to 30 nucleotides, or nucleotide analogs, whose sequence is complementary to a predetermined segment of the RNA, either freshly transcribed or the messenger (mRNA), critical to some viral function. It is believed that when an antisense oligonucleotide hybridizes to its target RNA, it either blocks translation or processing of the RNA or makes it susceptible to enzymatic degradation.

One problem with this approach has been the difficulty of getting the antisense oligonucleotide to its target RNA in sufficient concentration and for sufficient duration to be effective in shutting down the synthesis of undesired proteins, e.g. viral enzymes, coat proteins, and the like. The susceptibility of the phosphodiester linkage of the oligonucleotides to nuclease digestion is believed to be an important cause of this difficulty, and has prompted the development of a variety of nucleoside oligomers linked by nuclease-resistant analogs of the natural phosphodiester bond, e.g. Miller et al, U.S. Pat. No. 4,511,713 and Ts'o U.S. Pat. No. 4,469,863 (methyl-and arylphosphonates); Miro et al, Nucleic Acids Research, Vol. 17, pgs. 8207-8219 (1989) (phosphoroselenoates); Brill et al, J. Am. Chem. Soc., Vol. 111, pg. 2321 (1989) (phosphorodithioates); and Matsukura et al, Proc. Natl. Acad. Sci., Vol. 84, pgs. 7706-7710 (1987), and Gene, Vol. 72, pgs. 343-347 (1988) (phosphorothioates).

The phosphorothioate and phosphorodithioate analogs are especially promising because they are highly nuclease-resistant, have the same charge as natural oligonucleotides, and are taken up by cells in effective amounts.

Phosphorothioates are conveniently synthesized by automated DNA synthesizers using hydrogen phosphonate chemistry, which permits the phosphonate backbone to be sulfurized in a single step off of the automated synthesizer after synthesis. This is advantageous because the phosphonate moieties are sulfurized by exposure to elemental sulfur dissolved in an organic solvent. Since the sulfur readily precipitates out of solution, the off-column sulfurization avoids costly blockages of valves and tubing of the synthesizer by sulfur precipitates. A drawback of of this route of phosphorothioate synthesis is that coupling yields during chain elongation are typically lower than those obtained using phosphoramidite chemistry, Gaffney and Jones, Tett. Lett., Vol. 29, pgs. 2619-2622 (1988). The practical importance of high coupling yields is demonstrated by the synthesis of a 28-mer where a 99% coupling yield per step results in an overall yield of 76% ($0.99^{27}$), whereas a 96% yield per step results in an overall yield of only 33% ($0.96^{27}$).

Phosphoramidite chemistry, with coupling yields typically greater than 99%, would be a highly desirable approach to phosphorothioate and phosphorodithioate synthesis. However, the phosphite intermediates, which would be sulfurized, are unstable under the conditions of the detritylation step of the reaction cycle. This requires that the phosphite linkage be sulfurized after each coupling step. For practical purposes, such sulfurizations would have to be carried out on an automated synthesizer, but the sulfur precipitation problem discussed above precludes the use of any of the commercially available machines. Moreover, the sulfurization rate of the phosphites is relatively slow and suffers from side reactions that lead to increased contamination of the final product.

In view of the desire to employ phosphorothioate and phosphorodithioate analogs of oligonucleotides as pharmaceutical compounds, it would be advantageous to have available a method for sulfurizing that achieved the highest possible yields of completely sulfurized analogs and that was amenable for use with automated synthesizers, particularly with phosphoramidite and/or phosphorthioamidite chemistries.

SUMMARY OF THE INVENTION

The invention relates to a method of synthesizing sulfur-containing analogs of oligonucleotides, particularly but not exclusively, phosphorothioate and phosphorodithioate analogs. The method of the invention comprises the step of treating phosphorous(III) linkages of the intermediates of the desired analog with a thiophosphorus compound selected from the group defined by Formula I and Formula II to obtain the desired analog. In particular, when phosphoramidite chemistry is employed the phosphorous(III) linkage is a phosphite and the end product is a phosphorothioate, when phosphorothioamidite chemistry is employed the phosphorous(III) linkage is a thiophosphite and the end product is a phosphorodithioate, and when hydrogen phosphonate chemistry is employed the phosphorous(III) linkage is a hydrogen phosphonate diester and the end product is a phosphorothioate.

Preferably, the thiophosphorus compounds used in the invention are selected from the group consisting of thiophosphoric, dithiophosphoric, thiophosphinic, and dithiophosphinic acid polysulfides. More particularly, the thiophosphorus compounds defined by the formulas:

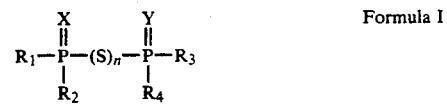

Formula I

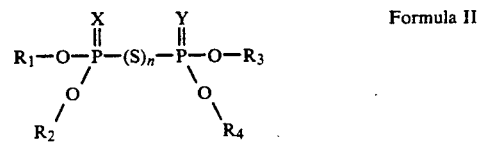

Formula II wherein:

X is oxygen or sulfur; and most preferably, X is sulfur.

Y is oxygen or sulfur; and most preferably, Y is sulfur.

n is within the range of 2-10, inclusive, and most preferably, n is 2.

$R_1$, $R_2$, $R_3$, and $R_4$ are inert side chains that can vary greatly in composition. Generally, they should not contain reactive groups that could lead to side reactions and inefficient sulfurization, and when taken together, they should permit the thiophosphorus compound to be soluble to an effective concentration. Preferably, $R_1$, $R_2$, $R_3$, and $R_4$ separately are alkyl, alkenyl, aryl, acyl, aralkyl, cycloalkyl, or cycloalkylalkyl containing up to 10 carbon atoms; halo-, nitro-, sulfo-, cyano-, lower alkoxy-substituted alkyl, alkenyl, aryl, acyl, aralkyl, cycloalkyl, or cycloalkylalkyl containing up to 10 carbon atoms; a heterocycle containing from 1 to 3 heteroatoms of nitrogen, oxygen, or sulfur, and from 2 to 8 carbon atoms; or a lower alkyl-, halo-, nitro-, sulfo-, cyano-, lower alkoxy-substituted heterocycle containing from 1 to 3 heteroatoms of nitrogen, oxygen, or sulfur, and from 2 to 8 carbon atoms. More preferably, $R_1$, $R_2$, $R_3$, and $R_4$ are separately lower alkyl; lower alkenyl; or cycloalkylalkyl, aryl or aralkyl containing up to 8 carbon atoms; halo-, nitro-, sulfo-, cyano-, lower alkoxy-substituted lower alkyl, lower alkenyl; or lower alkyl-, halo-, nitro-, sulfo-, cyano-, lower alkoxy-substituted aryl or aralkyl containing up to 8 carbon atoms; morpholinyl; thiomorpholinyl; piperidinyl; piperazinyl; or lower alkyl-, halo-, nitro-, sulfo-, cyano-, lower alkoxy-substituted morpholinyl; thiomorpholinyl; piperidinyl; piperazinyl. In further preference, $R_1$, $R_2$, $R_3$, and $R_4$ are separately methyl, ethyl, propyl, isopropyl, n-butyl, sec-butyl, tert-butyl, n-pentyl, cyclopentyl, cyclopentylmethyl, isopentyl, neopentyl, n-hexyl, neohexyl, isohexyl, cyclohexyl, cyclohexylmethyl, 2-ethylhexyl, betacyclopentylethyl; methyl-, ethyl-, methoxy-, nitro-, or halo-substituted phenyl; or methyl-, ethyl-, methoxy-, nitro- or halo-substituted benzyl. Preferably, the halo-substituents of the substituted phenyl or benzyl are chloro or bromo. Most preferably, $R_1$, $R_2$, $R_3$, and $R_4$ are separately methyl, ethyl, n-propyl, isopropyl, or 2-ethylhexyl.

The term "lower alkyl" as used herein denotes straight-chain, branched-chain, and cyclic alkyl groups containing from 1-8 carbon atoms, e.g. methyl, ethyl, propyl, isopropyl, tert-butyl, isobutyl, sec-butyl, neopentyl, tert-pentyl, cyclohexyl, and the like. Likewise, the term "lower alkenyl" as used herein denotes straight-chain, branched-chain, and cyclic alkenyl groups containing from 2 to 8 carbon atoms.

The term "oligonucleotide" as used herein includes linear oligomers of natural or modified nucleosides or of non-nucleosidic analogs linked by phosphodiester bonds or analogs thereof ranging in size from a few monomeric units, e.g. 2-3, to several hundred monomeric units. In particular, the term includes non-natural oligomers having phosphorus-containing linkages whose phosphorous(III) precursors are amenable to sulfurization, e.g. Takeshita et al, J. Biol. Chem., Vo. 282, pgs. 10171-10179 (1987); and Eapienis et al, pgs. 225-230 in, Bruzik and Stec, eds., *Biophosphates and Their Analogs--Synthesis, Structure, Metabolism, and Activity* (Elsevier, Amsterdam, 1986).

DETAILED DESCRIPTION OF THE INVENTION

The invention includes a method of synthesizing phosphorothioates and phosphorodithioates. An important feature of the invention is the step of reacting phosphorous III-containing moieties of oligonucleotide intermediates with a thiophosphorus compound selected from Formula I or Formula II to bring about sulfurization. Because the thiophosphorus compounds of Formulas I and II are efficient sulfurizing agents that do not precipitate out of solution, the invention is particularly useful in the automated synthesis of phosphorothioate and phosphorodithioate analogs of oligonucleotides by all the commercially viable approaches, including hydrogen phosphonate, phosphoramidite, or phosphorothioamidite chemistries.

Detailed procedures for the phosphoramidite, phosphorthioamidite, and hydrogen phosphonate methods of oligonucleotide synthesis are described in the following references, which are incorporated by reference: Caruthers et al, U.S. Pat. Nos. 4,458,066 and 4,500,707; Koester et al, U.S. Pat. No. 4,725,677; Matteucci et al, *J. Amer. Chem. Soc.*, Vol 103, pgs. 3185-3191 (1981); Caruthers et al, *Genetic Engineering*, Vol. 4, pgs. 1-17 (1981); Jones, chapter 2, and Atkinson et al, chapter 3, in Gait, ed., *Oligonucleotide Synthesis: A Practical Approach* (IRL Press, Washington, D.C., 1984); Froehler et al, *Tetrahedron Letters*, Vol. 27, Pgs. 469-472 (1986); Garegg et al, *Tetrahedron Letters*, Vol. 27, pgs. 4051-4054 and 4055-4058 (1986); Andrus et al, U.S. Pat. No. 4,816,571; Brill et al, J. Am. Chem. Soc., Vol. 111, pgs. 2321(1989); and Froehler et al, *Nucleic Acids Research*, Vol. 14, pgs. 5399-5407 (1986).

Thiophoshoric, dithiophosphoric, thiophosphinic, and dithiophosphinic acid disulfides of the invention are readily prepared by oxidation of the salts, e.g. triethylammonium, sodium, and the like, of the corresponding thiophosphoric, dithiophosphoric, thiophosphinic, or dithiophosphinic acids with oxidizing agents such as iodine, bromine, and the like. Methods of synthesis and properties of these disulfides are described in the following references which are incorporated by reference: Shishkov et al, *Nauch. Tr., Plovdivski Univ., Mat., Fiz., Khim., Biol.*, Vol. 10, pgs. 117-122 (1972); Almasi et al, *Monatsh Chem.*, Vol. 100, pgs. 798-805 (1969); Krawczyk et al, *Phosphorous Sulfur*, Vol. 9, pgs. 189-192 (1980); Komber et al, *Phosphorous Sulfur*, Vol. 35, pgs. 335-343 (1988); and Haegele et al, *Z. Naturforsch.*, Teil B, Vol. 29, pgs. 349-357 (1974). Many of the acid precursors to the above disulfides are commercially available materials which are used industrially as solvent extraction and floatation agents. Examples include bis(2,4,4-trimethylpentyl)-dithiophosphinic acid and bis(2,4,4-trimethylpentyl)-monothiophosphinic acid (American Cyanamide) and bis(n-propyl)-dithiophosphoric acid and bis(2-ethylhexyl)-dithiophosphoric acid disulfide (ELCO). The synthesis of the dithiophosphoric acid compounds involves the reaction of the appropriate alcohol with phosphorous pentasulfide. The reaction product mixture generally contains varying amounts of the bis(alkyl)-dithiophosphoric acid thioanhydride (monosulfide), bis(alkyl)-dithiophosphoric acid disulfide, and bis(alkyl)-dithiophosphoric acid polysulfides, as well as the bis(alkyl)-dithiophosphoric acid product. Although the bis(alkyl)-dithiophosphoric acid may be purified and then oxidized to the disulfide, the entire reaction product mixture may be oxidized to produce a mixture of monosulfides, disulfides, and polysulfides which comprises a useful sulfurizing reagent.

When employed as a sulfurizing agent in the hydrogen phosphonate approach, a thiophosphorus compound of the invention is delivered to the completed oligonucleotide chain in a suitable organic solvent, such as acetonitrile, pyridine, tetrahydrofuran, dichloromethane, or the like, in a concentration of between about 0.01M to about 2.0M. Preferably, the sulfurization is accomplished on an automated DNA synthesizer, e.g. an Applied Biosystems model 380B, or like machine.

Most preferably, the compounds of the invention are employed as a sulfurizing agents in the phosphoramidite or phosphorthioamidite approaches. A thiophosphorus compound of the invention is delivered to the growing oligomer as a separate step within each addition cycle. Generally, the addition cycles of these methods of synthesis involve the following steps: (1) deblocking a blocked functionality (usually a 5'-tritylated hydroxyl) on the growing correct-sequence chain, or on the initial monomer attached to a solid phase support, to form a reactive functionality (e.g. a 5'-hydroxyl), (2) reacting an appropriately blocked and protected nucleoside phosphoramidite or phosphorthioamidite monomer or analog thereof (usually in the presence of an activator, e.g. tetrazole) with the reactive functionality of the growing correct-sequence chain, (3) capping unreacted reactive functionalities, and (4) oxidizing the newly formed phosphorous(III) linkage to form the naturally occurring pentacoordinate state. The sequence of above steps (3) and (4) can be reversed. The term "protected" in reference to monomer, particularly nucleoside phosphoramidites or phosphorthioamidites, means that moieties such as exocyclic nitrogens, 2'-hydroxyls, oxygens bonded to the phosphorous, or the like, have protection groups (usually base-labile) attached which are removed after synthesis is completed, e.g. as those described in Koester et al (cited above), or in Molko et al, European patent publication no. 241,363 dated 14 Oct. 1987. The term is also meant to include monomers which may not have moieties requiring protective groups, e.g. some nucleoside analogs, abasic nucleosides, and the like. In the method of the invention, the thiophosphorus compounds defined by Formulas I and II are employed as sulfurizing agents in place of the oxidation step. Preferably, such a thiophosphorus compound is delivered to the growing oligomer in a suitable organic solvent, such as acetonitrile, tetrahydrofuran, dichloromethane, or the like, in a concentration of between about 0.01M to about 2.0M. Preferably, the step of sulfurizing with a thiophosphorus compound of Formula I or II is accomplished on an automated DNA synthesizer. In both approaches a wide variety of reaction temperatures may be used. Preferably, the sulfurization is carried out at a temperature in the range of 0° C. to 100° C., and more preferably, in the range of 15° C. to 60° C.

EXAMPLE 1

Synthesis of Bis(diisopropoxyphosphinothioyl) disulfide (O,O-diisopropylphosphorodithioic acid disulfide)

PART A: Into 50 ml of absolute isopropanol was added at room temperature with stirring 20 g of phosphorous pentasulfide (Fluka) in small portions. Hydrogen sulfide is release and needs to be trapped. The reaction mixture was stirred at room temperature for about 3 hours until a clear, transparent liquid was obtained. This solution was concentrated by rotary evaporation and the residue was distilled with a 30 cm Vigroux column, collecting the fraction at 57°–58° C. under 0.02 mm Hg to give 34 g of O,O-diisopropylphosphorodithioic acid.

PART B: To a stirred solution of 19.4 of O,O-diisopropylphosphorothioic acid in 30 ml of methylene chloride, cooled in an ice bath, was added dropwise 9.3 g (12.6 ml) of triethylamine. This solution was cooled below 5° C. and 12.5 g of iodine was added in small portions, maintaining the temperature below 10° C. After 0.5 hours of stirring, the reaction mixture was extracted three times with water, dried over anhydrous magnesium sulfate, and filtered. Ethanol (100 ml) was added to the solution which was then concentrated by rotary evaporation, during which pale-yellow crystalline bis(diisopropoxyphosphinothioyl) disulfide was formed. This material was collected by filtration and washed with cold ethanol and dried to give 16.7 g of pure product. The $^{31}$P NMR spectra was a single peak at 82.6 ppm ($H_3PO_4$, external reference). M.P. 92°–93° C.

EXAMPLE 2

Synthesis of a 27-base Phosphorothioate Oligonucleotide Using O,O-Diisopropylphosphorodithioic Acid Disulfide as a Sulfurizing Agent A 27-base phosphorothioate oligonucleotide, 5'-TCGTCTTGTCCCGTCATCGTTGCCCCT-3' was synthesized by the phosphoramidite method on an automated synthesizer (model 380B Applied Biosystem, Foster City, Calif.). The standard synthesis protocol was followed, except that in place of the oxidation step a sulfurization step was substituted, and this step preceded the capping step. In other words, the synthesis consisted of repeated cycles of detritylation, coupling, sulfurization, and capping. Separation of the final product from the synthesis column and purification were accomplished by standard means. The sulfurization step was accomplished by exposing the growing chain to a 0.2M solution of O,O-diisopropylphosphorodithioic acid disulfide in pyridine for 1 minute at room temperature.

The yield of trityl cation released during the detritylation steps averaged 99%. The trityl yield is a both a measure of coupling efficiency and a measure of the extent of sulfurization, since non-sulfurized (or oxidized) trivalent phosphorous linkages in the oligonucleotide are labile to cleavage during detritylation.

The 27-mer was cleaved from the support and deprotected with concentrated ammonium hydroxide at 55° C. for 6 hours. The trityl-on oligonucleotide was isolated by HPLC, detritylated, and precipitated as the sodium salt. The $^{31}$P-NMR spectra (JEOL, 36.5 MHz, ppm vs $H_3PO_4$ external reference) of the product showed greater than 98.5% sulfur incorporation (55.1 ppm) with less than 1.5% oxygen incorporation (−1.1 ppm).

EXAMPLE 3

Synthesis of a poly-A 19-mer phosphorothioate oligonucleotide using O,O-diisopropyl-phoshorodithioic acid disulfide as a sulfurizing agent A poly-A 19-mer phosphorothioate oligonucleotide was synthesized following the same protocol as used in example 2. The yield of trityl cation averaged 98.5% per detritylation step. $^{31}$P-NMR of the product indicated 99% sulfur incorporation and 1% oxygen incorporation.

EXAMPLE 4

Synthesis of O,O-diisopropyl-phosphorothioic acid disulfide

A solution of 25.6 g of $S_8$ and 117 ml of triethylamine in 750 ml of carbon disulfide was added to 132.8 g of neat diisopropyl phosphite. After several hours of stirring at ambient temperature the reaction mixture was concentrated by rotary evaporation. The O,O-diisopropyl-phosphorothioic acid product was dissolved in 750 ml of methylene chloride and stirred while the solution was cooled in an ice bath. To this solution was added 20.5 ml of bromine dropwise. The solution was allowed to stir an additional hour at ambient temperature, and then extracted three times with deionized water. The organic phase was then dried with anhydrous sodium sulfate and filtered. The filtrate was concentrated by rotary evaporation, and dried overnight under reduced pressure, to yield 137 g of O,O-diisopropyl-phosphorothioic acid disulfide (87% yield). The $^{31}$P-NMR spectra of the product dissolved in methylene chloride consisted of a single peak at 18.1 ppm vs. and external standard of phosphoric acid.

EXAMPLE 5

Synthesis of a 14-base phosphorothioate oligonucleotide using O,O-diisopropyl-phosphorothioic acid disulfide as the sulfurizing agent A 14-base phosphorothioate oligonucleotide, 5'-CGCTTCTTCCTGCC, was synthesized as in example 2, with the exception that the sulfurization step was carried out using a 0.2M solution of O,O-diisopropyl-phosphorothioic acid disulfide in 2:1 pyridine:acetonitrile for 10 minutes at ambient temperature. The yield of trityl cation released during the detritylation step averaged 99%. The $^{31}$P-NMR spectra of the 14-mer showed 92% sulfur incorporation and 8% oxygen incorporation.

EXAMPLE 6

Synthesis of O,O-di-2-ethylhexyl-phosphorodithioic acid disulfide

A solution of 177 g of O,O-di-2-ethylhexylphosphorodithioic acid (Elco L-21612) in 400 ml of methylene chloride was cooled in an ice bath and 73.5 ml of triethylamine was added dropwise with stirring. While continuing to cool the stirred solution in an ice bath 61.5 g of iodine was added in small portions. The reaction mixture was allowed to stir at ambient temperature an additional 30 minutes and then was extracted once with deionized water and then twice with aqueous brine. The organic phase was dried with anhydrous sodium sulfate, filtered, and then concentrated by rotary evaporation. The product was dried overnight under reduced pressure to yield 171 g (97% yield) of O,O-di-2-ethylhexyl-phosphorodithioic acid disulfide as a yellow oil. The $^{31}$P-NMR spectra of the product consisted of a resonance at 86.0 ppm corresponding to the desired product and another resonance at 79.0 ppm (4%) corresponding to bis(O,O-di-2-ethylhexyl-phosphorodithioic acid thioanhydride (the monsulfide), which was present as an impurity in the starting material.

EXAMPLE 7

Synthesis of a 27-mer phsphorothioate oligonucleotide using O,O-di-2-ethylhexyl-phosphorodithioic acid disulfide as the sulfurizing agent A 27-base phphorothioate oligonucleotide, 5'-TCGTCGCTTCTCTGCTTCCGTCTGCC-3', was synthesized following the same protocol as used in example 2, with the following exception. The sulfurization step was carried out using O,O-di-2-ethylhexylphosphorodithioic acid disulfide which was 0.2M in a mixture of 20 parts by volume pyridine and 31.5 parts acetonitrile. The sulfurization step was carried out at room temperature for 15 minutes. The yield of trityl cation averaged 98% per detritylation step. $^{31}$P-NMR of the product indicated 99% sulfur incorporation and 1% oxygen incorporation.

EXAMPLE 8

Synthesis of bis(2,4,4-trimethylpentyl)-dithiophosphinic acid disulfide

A solution of 161 g of bis(2,4,4-trimethylpentyl)dithiophosphinic acid (Cyanex 301, American Cyanamide, 77% pure) in 400 ml of methylene chloride was cooled in an ice bath and 73.2 ml of triethylamine was added dropwise with stirring. While continuing to cool the stirred solution in an ice bat 50.7 g of iodine was added in small portions. The reaction mixture was allowed to stir an additional 30 minutes at ambient temperature after which it was extracted once with deionized water, then twice with aqueous brine. The organic phase was dried with anhydrous sodium sulfate, filtered, and then concentrated by rotary evaporation. The product was dried overnight under reduced pressure to yield 158.7 g of crude product. The $^{31}$P-NMR spectra of the crude product indicated the presence of a complex mixture. The desired bis(2,4,4-trimethylpentyl)-dithiophosphinic acid disulfide comprised about half of the mixture (a multiplet at ca. 80 ppm vs. phosphoric acid external standard). Impurities included the monothiophosphinic acid disulfide and the mixed disulfide of the monothiophosphinic acid and the dithiophosphinic acid. The monothiophosphinic acid was present as an impurity in the starting material.

EXAMPLE 9

Synthesis of an 18-mer phosphorothioate oligonucleotide using bis(2,4,4-trimethylpentyl)-dithiophosphinic acid as a sulfurizing agent An 18-mer phosphorothioate oligonucleotide, 5'-TCTCTGCTTCCGTCTGCC-3', was synthesized using the same protocol as used in example 2, with the following exception. The sulfurization step was carried out using a solution of 137.9 g of crude bis(2,4,4-trimethylpentyl)dithiophosphinic acid disulfide in a mixture of 360 ml of acetonitrile and 100 ml of pyridine. The sulfurization step was carried out for 15 minutes at ambient temperature. The yield of trityl cation averaged 97.3% per detritylation step. The $^{31}$P-NMR spectra of the 18-mer showed 98% sulfur incorporation and 2% oxygen incorporation.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

What is claimed is:

1. A method of synthesizing an oligonucleotide phosphorothioate or phosphorodithioate of a predetermined sequence, the method comprising the steps of:
   (a) providing a protected nucleoside or analog thereof attached to a solid phase support, the protected nucleoside or analog thereof having a blocked hydroxyl;
   (b) deblocking the blocked hydroxyl to form a free hydroxyl;
   (c) reacting with the free hydroxyl a blocked protected nucleoside phosphoramidite or phosphorthioamidite monomer or analog thereof to form a correct-sequence chain having a phosphorous(III) linkage and a blocked hydroxyl;
   (d) sulfurizing the phosphorous(III) linkage by exposing the correct-sequence chain to a thiophosphorus compound selected from the group consisting of thiophosphoric acid polysulfide dithiophosphoric acid polysulfide, and dithiophosphinic acid polysulfide;
   (e) repeating steps (b) through (d) until the oligonucleotide phosphorothioate or phosphorodithioate of the predetermined sequence is obtained.

2. The method of claim 1 wherein said thiophosphorus compound is defined by the formulas:

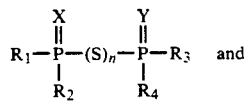
and
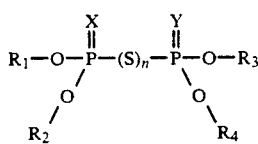

wherein:
X is oxygen or sulfur;
Y is oxygen or sulfur;
n is within the range of 2–10, inclusive; and
$R_1$, $R_2$, $R_3$, and $R_4$ are separately hydrogen; alkyl alkenyl, aryl, acyl, aralkyl, cycloalkyl, or cycloalkylalkyl containing up to 10 carbon atoms; halo-, nitro-, sulfo-, cyano-, lower alkoxy-substituted alkyl, alkenyl, aryl, acyl, aralkyl, cycloalkyl, or cycloalkylalkyl containing up to 10 carbon atoms; a heterocycle containing from 1 to 3 heteroatoms of nitrogen, oxygen, or sulfur, and from 2 to 8 carbon atoms; or a lower alkyl-, halo-, nitro-, sulfo-, cyano-, lower alkoxy-substituted heterocycle containing from 1 to 3 heteroatoms of nitrogen, oxygen, or sulfur, and from 2 to 8 carbon atoms.

3. The method of claim 2 further including the step of capping unreacted free hydroxyls after said step of sulfurizing.

4. The method of claim 3 further including the step of cleaving said oligonucleotide phosphorothioate or phosphorodithioate from said solid phase support.

5. The method of claim 4 wherein said blocked hydroxyl is a tritylated 5'-hydroxyl of said correct-sequence chain or of said protected nucleoside or analog thereof.

6. The method of claim 5 wherein:
X is sulfur;
Y is sulfur;
n is 2; and
$R_1$, $R_2$, $R_3$, and $R_4$ are separately hydrogen; lower alkyl; lower alkenyl; or cycloalkylalkyl, aryl or aralkyl containing up to 8 carbon atoms; halo-, nitro-, sulfo-, cyano-, lower alkoxy-substituted lower alkyl, lower alkenyl; or lower alkyl-, halo-, nitro-, sulfo-, cyano-, lower alkoxy-substituted aryl or aralkyl containing up to 8 carbon atoms; morpholinyl; thiomorpholinyl; piperidinyl; piperazinyl; or lower alkyl-, halo-, nitro-, sulfo-, cyano-, lower alkoxy-substituted morpholinyl, thiomorpholinyl, piperidinyl, piperazinyl.

7. The method of claim 6 wherein $R_1$, $R_2$, $R_3$, and $R_4$ are separately hydrogen, methyl, ethyl, propyl, isopropyl, n-butyl, sec-butyl, tert-butyl, n-pentyl, cyclopentyl, cyclopentylmethyl, isopentyl, neopentyl, n-hexyl, neohexyl, isohexyl, cyclohexyl, cyclohexylmethyl, 2-ethylhexyl, beta-cyclopentylethyl; methyl-, ethyl-, methoxy-, nitro-, or halo-substituted phenyl; or methyl-, ethyl-, methoxy-, nitro- or halo-substituted benzyl.

8. The method of claim 7 wherein $R_1$, $R_2$, $R_3$, and $R_4$ are separately methyl, ethyl, n-propyl, isopropyl, or 2-ethylhexyl.

9. The method of claim 8 wherein said thiophosphorus compound is defined by the formula:

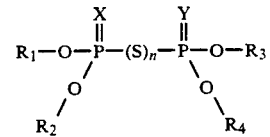

wherein:
X is sulfur;
Y is sulfur;
n is 2; and
$R_1$, $R_2$, $R_3$, and $R_4$ are separately methyl, ethyl, n-propyl, isopropyl, or 2-ethylhexyl.

10. The method of claim 9 wherein $R_1$, $R_2$, $R_3$, and $R_4$ are isopropyl.

11. In a method for synthesizing a sulfurized oligonucleotide, the method of the type wherein nucleosides are added stepwise to a growing oligonucleotide chain attached to a solid phase support and wherein phosphorous(III) linkages of the growing oligonucleotide chain are sulfurized, an improvement comprising:
   sulfurizing the phosphorous(III) linkages of the growing oligonucleotide chain by exposing the growing oligonucleotide chain to a compound selected from the group consisting of thiophosphoric acid polysulfide, dithiophosphoric acid polysulfide, thiophosphinic acid polysulfide, and dithiophosphinic acid polysulfide.

12. The method of claim 11 wherein said thiophosphorus compound is defined by the formula:

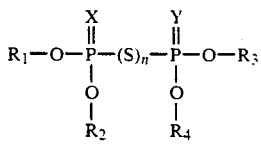

wherein:
X is oxygen or sulfur;
Y is oxygen or sulfur;
n is within the range of 2–10, inclusive; and
$R_1$, $R_2$, $R_3$, and $R_4$ are separately hydrogen; alkyl, alkenyl, aryl, acyl, aralkyl, cycloalkyl, or cycloalkylalkyl containing up to 10 carbon atoms; halo-, nitro-, sulfo-, cyano-, lower alkoxy-substituted alkyl, alkenyl, aryl, acyl, aralkyl, cycloalkyl, or cycloalkylalkyl containing up to 10 carbon atoms; a heterocycle containing from 1 to 3 heteroatoms of nitrogen, oxygen, or sulfur, and from 2 to 8 carbon atoms; or a lower alkyl-, halo-, nitro-, sulfo-, cyano-, lower alkoxy-substituted heterocycle containing from 1 to 3 heteroatoms of nitrogen, oxygen, or sulfur, and from 2 to 8 carbon atoms.

13. The method of claim 12 wherein:
X is sulfur;
Y is sulfur;
n is 2; and
$R_1$, $R_2$, $R_3$, and $R_4$ are separately hydrogen; lower alkyl; lower alkenyl; or cycloalkylalkyl, aryl, or aralkyl containing up to 8 carbon atoms; halo-, nitro-, sulfo-, cyano-, lower alkoxy-substituted lower alkyl, alkenyl, lower alkenyl; or lower alkyl-, halo-, nitro-, sulfo-, cyano-, lower alkoxy-substituted aryl or aralkyl containing up to 8 carbon atoms; morpholinyl; thiomorpholinyl; piperidinyl; piperazinyl; or lower alkyl-, halo-, nitro-, sulfo-, cyano-, lower alkoxy-substituted morpholinyl, thiomorpholinyl, piperidinyl, or piperazinyl.

14. The method of claim 13 wherein $R_1$, $R_2$, $R_3$, and $R_4$ separately are hydrogen, methyl, ethyl, propyl, isopropyl, n-butyl, sec-butyl, sec-butyl, tert-butyl, n-pentyl, cyclopentyl, cyclopentylmethyl, isopentyl, neopentyl, n-hexyl, neohexyl, isohexyl, cyclohexyl, cyclohexylmethyl, 2-ethylhexyl, beta-cyclopentylethyl; methyl-, ethyl-, methoxy-, nitro-, or halo-substituted phenyl; or methyl-, ethyl-, methoxy-, nitro- or halo-substituted benzyl.

15. The method of claim 14 wherein $R_1$, $R_2$, $R_3$, and $R_4$ are separately methyl, ethyl, n-propyl, isopropyl, or 2-ethylhexyl.

16. The method of claim 15 wherein $R_1$, $R_2$, $R_3$, and $R_4$ are isopropyl.

17. The method of claim 15 wherein said step of sulfurizing includes forming phosphorothioate or phosphorodithioate linkages from said phosphorous(III) linkages.

* * * * *

UNITED STATES PATENT AND TRADEMARK OFFICE
CERTIFICATE OF CORRECTION

PATENT NO. : 5,151,510
DATED : September 29, 1992
INVENTOR(S) : Stec et al

It is certified that error appears in the above-indentified patent and that said Letters Patent is hereby corrected as shown below:

On the title page, and col 1, line 2, delete "SYNETHESIZING" and replace with —SYNTHESIZING—.

Signed and Sealed this

Twenty-third Day of May, 1995

Attest:

BRUCE LEHMAN

Attesting Officer      Commissioner of Patents and Trademarks